United States Patent [19]

Dotolo et al.

[11] Patent Number: 5,465,685
[45] Date of Patent: Nov. 14, 1995

[54] ANIMAL COAT DEODORIZER AND INSECT REPELLENT

[75] Inventors: John Dotolo, Clearwater; Ronnie E. Bayless, Plat City, both of Fla.

[73] Assignee: Citra Science Ltd., Largo, Fla.

[21] Appl. No.: 285,124

[22] Filed: Aug. 2, 1994

[51] Int. Cl.⁶ .......................... A01N 25/00; A01K 13/00
[52] U.S. Cl. .................... 119/159; 119/156; 424/405; 514/919
[58] Field of Search ...................... 119/156, 159; 424/405; 514/919

[56] References Cited

U.S. PATENT DOCUMENTS

| | | | |
|---|---|---|---|
| 4,379,168 | 4/1983 | Dotolo | 424/356 |
| 4,933,371 | 6/1990 | Hink et al. | 514/739 |
| 5,079,063 | 1/1992 | Plischke et al. | 428/95 |
| 5,164,416 | 11/1992 | Nagai et al. | 514/763 |
| 5,204,016 | 4/1993 | Hamilton et al. | 252/162 |

*Primary Examiner*—Robert P. Swiatek
*Attorney, Agent, or Firm*—Donald R. Fraser

[57] ABSTRACT

A non-toxic, biodegradable sprayable liquid which is effective as a deodorizer and insect repellent for livestock and livestock enclosures consists of d-limonene, a surfactant, hexylene glycol, triethanolamine, and water.

21 Claims, No Drawings

ANIMAL COAT DEODORIZER AND INSECT REPELLENT

FIELD OF THE INVENTION

This invention relates generally to a formulation for an insect repellent and animal coat deodorizer. More particularly, the invention is directed to a formulation for a sprayable liquid containing d-limonene which can be applied to the coats of animals to repel barn flies and which additionally deodorizes the animals' coats and the barn atmosphere.

BACKGROUND OF THE INVENTION

Various commercial products are available for deodorizing the coats of animals and the barns and stables in which they are kept. Some of these products additionally function as an insect repellent for flies and other similar pests. Such products generally irritate the skin of the livestock on which they are applied. Moreover, such products can be toxic to smaller livestock or domesticated pets.

It would be desirable to formulate a sprayable liquid which could be applied to the coats of animals or atomized into the air within a livestock enclosure to function as an insect repellent and deodorizer, and which would be non-toxic and biodegradable.

SUMMARY OF THE INVENTION

Accordant with the present invention a non-toxic, biodegradable sprayable liquid which functions as an insect repellent and deodorizer has surprisingly been discovered. The sprayable liquid consists of d-limonene, a surfactant, hexylene glycol, triethanolamine, and water. This formulation may be applied directly to the coats of livestock, to condition and deodorize same, or may be diluted and atomized into the air within a livestock enclosure to deodorize the atmosphere. Moreover, the neat and diluted sprayable liquids repel insects from the livestock coats and barn atmosphere.

DETAILED DESCRIPTION OF THE PREFERRED EMBODIMENT

The formulating of the present invention of a precise combination of d-limonene, a surfactant, hexylene glycol, triethanolamine, and water.

D-limonene is a terpene which occurs naturally in all living plants. It is a nonocyclic unsaturated terpene which is generally a by-product of the citrus industry, derived from the distilled rind oils of oranges, grapefruits, lemons, and the like. A discussion of d-limonene and its derivation from numerous sources is set forth in Kesterson, J. W., "Florida Citrus Oil," Institute of Food and Agricultural Sciences, University of Florida, December 1971. D-Limonene is commercially available from Florida Chemical Company and from SMC Glidco Organics. D-limonene is present in the inventive formulation at a concentration from about 0.5 to about 40 weight percent. Preferably, the concentration is from about 5 to about 15 weight percent. Most preferably, the concentration is about 10 weight percent.

The formulation of the present invention includes a surfactant at a concentration from about 3.5 to about 41 weight percent. This component allows the d-limonene to be emulsified in the aqueous sprayable liquid by reducing the surface tension between the d-limonene and the water, thereby producing a stable mixture of immiscible liquids. Examples of surfactants include, without limitation, carboxylates, polyalrylene oxides, carboxylic acid eaters, quaternary ammonium salts, and the like. Such surfactants as well as many others are well-known in the industry to those ordinarily skilled in the art. Surfactants are described more fully in Kirk-Othmer, "Carcise Encyclopedia of Chemical Technology," John Wiley and Sons, 1985 at pages 1142–1146. A preferred surfactant is the proprietary blend of surfactants contained in RHODATERGE MULTIGREEN, a product of Rhone-Poulenc of Cranbury, N.J. The surfactant is preferably present in the inventive sprayable liquid at a concentration from about 13.5 to about 27.5 weight percent.

Hexylene glycol is present in the formulation of the present invention at a concentration from about 1.5 to about 19 weight percent. Preferably, the concentration ranges from about 0.2 to about 0.8 weight percent. The triethanolamine acts as a humectant and softening agent, which is important in conditioning the coats of the animals to which the inventive formulation is applied. Moreover, it assists in emulsifying the liquid mixture.

Water constitutes the balance of the sprayable liquid formulation of the present invention.

The ingredients are combined and mixed together in conventional mixing apparatus, to prepare a sprayable liquid insect repellent and deodorizer which may then be applied to the coats of animals. The formulation may be sprayed directly onto individual animals or changed to a livestock wall-through spray application system. The inventive formulation additionally conditions the coats of the animals to which it is applied.

Moreover, the formulation of the present invention may be diluted with water (one part by weight of the formulation with up to about fifteen parts by weight water) to produce a barn environment insect repellent. The diluted formulation may be sprayed into the barn environment by conventional fogging equipment, to effective repel insects and to neutralize the malodorousness of the barn atmosphere.

The neat and diluted formations of the present invention have been found to be particularly useful for conditioning and deodorizing the coats of horses, and deodorizing horse stall environs, while at the same time repelling flies and other insects.

EXAMPLES

The following ingredients are mixed together in the approximately weigh percentages indicated, to form a sprayable liquid insect repellent and deodorizer, according to the present invention. Additionally, these formulations are mixed with approximately fourteen parts by weight water, to prepare an effective spray for deodorizing a livestock barn.

TABLE 1

| | Spray Formulations | |
|---|---|---|
| Ingredient | Example 1 | Example 2 |
| d-limonene (1) | 10 | 10 |
| surfactant (2) | 13.5 | 27.5 |
| hexylene glycol (2) | 6.5 | 13 |
| triethanolamine (2) | 0.4 | 0.8 |
| water | 69.6 | 48.7 |

(1) GLIDSAFE, from SMC Glidco Organics.
(2) Contained in RHODATERGE MULTIGREEN, from Rhone-Poulene.

These Examples may be repeated with similar success by substituting the generically or specifically described ingredients and/or concentrations recited herein for those used in the preceding Examples.

From the foregoing description, one ordinarily skilled in the art can easily ascertain the essential characteristics of the invention and, without departing from its spirit or scope, can make various changes and modifications in the invention to adapt it to various usages and conditions.

What is claimed is:

1. A sprayable liquid insect repellent and deodorizer, consisting of:

from about 0.5 to about 40 weight percent d-limonene;

from about 3.5 to about 41 weight percent surfactant;

from about 1.5 to about 19 weight percent hexylene glycol;

from about 0.1 to about 1.2 weight percent triethanolamine; and the balance water.

2. The sprayable liquid according to claim 1, wherein the d-limonene concentration ranges from about 5 to about 15 weight percent.

3. The sprayable liquid according to claim 2, wherein the d-limonene concentration is about 10 weight percent.

4. The sprayable liquid according to claim 1, wherein the surfactant concentration ranges from about 13.5 to about 27.5 weight percent.

5. The sprayable liquid according to claim 1, wherein the hexylene glycol concentration ranges from about 6.5 to about 13 weight percent.

6. The sprayable liquid according to claim 1, wherein the triethanolamine concentration ranges from about 0.2 to about 0.8 weight percent.

7. A sprayable liquid insect repellent and deodorizer, consisting of:

from about 5 to about 15 weight percent d-limonene;

from about 13.5 to about 27.5 weight percent surfactant;

from about 6.5 to about 13 weight percent hexylene glycol;

from about 0.2 to about 0.8 weight percent triethanolamine; and the balance water.

8. The sprayable liquid according to claim 7, wherein the d-limonene concentration is about 10 weight percent.

9. A method of conditioning and deodorizing the coats of livestock and repelling insects therefrom, comprising:

preparing a sprayable liquid, consisting of from about 0.5 to about 40 weight percent d-limonene, from about 3.5 to about 41 weight percent surfactant, from about 1.5 to about 19 weight percent hexylene glycol, from about 0.1 to about 1.2 weight percent triethanolamine, and the balance water; and applying the sprayable liquid to the coat of an animal.

10. The method according to claim 9, wherein the concentration of d-limonene in the sprayable liquid ranges from about 5 to about 15 weight percent.

11. The method according to claim 10, wherein the concentration of d-limonene in the sprayable liquid is about 10 weight percent.

12. The method according to claim 9, herein the concentration of surfactant in the sprayable liquid ranges from about 13.5 to about 27.5 weight percent.

13. The method according to claim 9, wherein the concentration of hexylene glycol in the sprayable liquid ranges from about 6.5 to about 13 weight percent.

14. The method according to claim 9, wherein the concentration of triethanolamine in the sprayable liquid ranges from about 0.2 to about 0.8 weight percent.

15. A method for deodorizing and repelling insects from the air within a livestock barn, comprising:

preparing a sprayable liquid, consisting of from about 0.5 to about 40 weight percent d-limonene, from about 3.5 to about 41 weight percent surfactant, from about 1.5 to about 19 weight percent hexylene glycol, from about 0.1 to about 1.2 weight percent triethanolamine, and the balance water, diluting the sprayable liquid by mixing same with water; and atomizing the diluted sprayable liquid into the air within the livestock barn.

16. The method according to claim 15, wherein the concentration of d-limonene in the sprayable liquid ranges from about 5 to about 15 weight percent.

17. The method according to claim 16, wherein the concentration of d-limonene in the sprayable liquid is about 10 weight percent.

18. The method according to claim 15, wherein the concentration of surfactant in the sprayable liquid ranges from about 13.5 to about 27.5 weight percent.

19. The method according to claim 15, wherein the concentration of hexylene glycol in the sprayable liquid ranges from about 6.5 to about 13 weight percent.

20. The method according to claim 15, wherein the concentration of triethanolamine in the sprayable liquid ranges from about 0.2 to about 0.8 weight percent.

21. The method according to claim 15, wherein the sprayable liquid is diluted with up to about fifteen parts by weight water.

* * * * *